United States Patent
Korb et al.

(10) Patent No.: US 6,281,383 B1
(45) Date of Patent: Aug. 28, 2001

(54) PROCESS FOR THE PREPARATION OF α,α-DIMETHYLPHENYLACETIC ACID FROM α,α-DIMETHYLBENZYL CYANIDE UNDER NORMAL PRESSURE

(75) Inventors: Gerhard Korb, Hainburg; Hans-Wolfram Flemming, Usingen; Rudolf Lehnert, Mainz; Wolfgang Rybczynski, Hünfelden-Ohren, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/404,811

(22) Filed: Sep. 24, 1999

(30) Foreign Application Priority Data

Sep. 26, 1998 (DE) .............................. 198 44 225

(51) Int. Cl.[7] .................................. C07C 53/134
(52) U.S. Cl. ............................................. 562/496
(58) Field of Search ............................ 562/496

(56) References Cited

FOREIGN PATENT DOCUMENTS

132658 * 10/1978 (DE) .
31 17 510 A1   2/1982 (DE) .

OTHER PUBLICATIONS

Buckle, D.R. et al., "Synthesis and Antiallergic Activity of 2–Hydroxy–3–nitro–1,4–naphthoquinones", Journal of Medicinal Chemistry, vol. 20, No. 8, p. 1059–1064, (1977).

Fujio, M. et al., "Substituent Effect on the Acetolysis of Neophyl p–Bromobenzenesufonates", Memoirs of the Faculty of Science, Kyushu University, Ser. C, vol. 14(2), p. 319–332, (1984).

Chemical Abstracts, vol. 64, No. 12, Makosza et al., "Reactions of Organic Anions. III. Synthesis of Phenyl–dialkylacetonitriles," XP002128783 (Jun. 6, 1966).

* cited by examiner

*Primary Examiner*—Paul J. Killos
(74) *Attorney, Agent, or Firm*—Finnegan, Henderson, Farabow, Garrett & Dunner, L.L.P.

(57) ABSTRACT

A process for obtaining α,α-dimethylphenylacetic acid wherein α,α-dimethylbenzyl cyanide is reacted in the presence of sodium hydroxide, water and a $C_4$- and/or $C_5$-alcohol at temperatures above about 100° C. and the α,α-dimethylphenylacetic acid is obtained by acidification.

16 Claims, No Drawings

PROCESS FOR THE PREPARATION OF α,α-DIMETHYLPHENYLACETIC ACID FROM α,α-DIMETHYLBENZYL CYANIDE UNDER NORMAL PRESSURE

This application claims the benefit of priority to German patent application serial no. 19844225.4, filed on Sep. 26, 1998, which priority document is incorporated by reference herein.

A process for preparation of α,α-dimethylphenylacetic acid from α,α-dimethylbenzyl cyanide is known. That preparation is described for instance in THE JOURNAL OF MEDICAL CHEMISTRY, 1977, volume 20, No. 8, page 1063. In this process, 2-phenyl-2-methylpropionic acid nitrile (α,α-dimethylbenzyl cyanide) is stirred in a solution of KOH (fivefold molar excess) and methanol in an autoclave at 140 to 150° C. under pressure for 20 hours, and the reaction mixture is then concentrated under reduced pressure, diluted with water, and acidified. The α,α-dimethylphenylacetic acid obtained as white crystals is then purified by an expensive purification process: filtration and recrystallization from ethanol. An α,α-dimethylphenylacetic acid with a melting point of 80° C. is obtained by this process, with a theoretical yield of 90%.

Our own experiments in which 2-phenyl-2-methylpropionic acid nitrile (α,α-dimethylbenzyl cyanide) was reacted in mixtures of n-butanol, water and KOH (threefold molar excess) at about 125° C. for 22 hours also did not lead to a complete hydrolysis of the nitrile employed. The corresponding amide intermediate was, furthermore, also found in amounts of 2%. Depletion of this intermediate would necessitate an additional purification step in order to obtain the desired α,α-dimethylphenylacetic acid of high purity.

Our own experiments in mixtures of n-butanol, water, and lithium hydroxide indicated only the formation of about 1% of the amide intermediate after a hydrolysis time of 4 hours at about 100° C. (under reflux). No hydrolysis up to the formation of the carboxylic acid was detected.

Further experiments of our own in 50% strength aqueous potassium or sodium hydroxide solution (threefold molar excess) at 125° C. with vigorous stirring showed the following analytical results after a reaction time of 20 hours:

| | | | |
|---|---|---|---|
| Potassium hydroxide solution: | nitrile 0.4% | Amide 51% | carboxylic acid 47% |
| Sodium hydroxide solution: | nitrile 62% | Amide 34% | carboxylic acid 2.7% |

The hydrolysis reaction with the stronger base, potassium hydroxide, proceeded much more rapidly than that with the weaker base, sodium hydroxide. Hence, our experiments indicated the following rates of hydrolysis therefore resulted: LiOH<NaOH<KOH.

It has now been found that the nitrile can be hydrolyzed to the carboxylic acid in a very short time under normal pressure in a mixture of a $C_4$- or $C_5$-alcohol, water and NaOH. Accordingly, the object of the invention is therefore to provide in high yields, by modification of the process conditions, an α,α-dimethylphenylacetic acid which is substantially free from 2-phenyl-2-methylpropionic acid nitrile (α,α-dimethylbenzyl cyanide) and 2-phenyl-2-methylpropionic acid amide.

The object is achieved by carrying out the reaction of α,α-dimethylbenzyl cyanide in the presence of sodium hydroxide, water, and a $C_4$-or $C_5$-alcohol at temperatures above 100° C. and then obtaining the α,α-dimethylphenylacetic acid by acidification. Additional purification steps are no longer necessary.

The invention therefore relates to a process for obtaining the compound of the formula I:

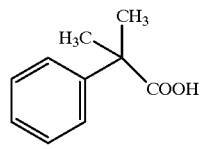

(I)

which comprises reacting a compound of the formula II:

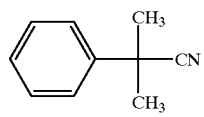

(II)

in the presence of water, sodium hydroxide, and a $C_4$-alcohol or $C_5$-alcohol at temperatures of more than about 100° C. to give the corresponding carboxylic acid salt, and then obtaining the compound of the formula I by addition of an acid.

In the preparation of the compound of the formula I, a procedure is followed in which the $C_4$- or $C_5$-alcohol, water, the sodium hydroxide, and the compound of the formula II (α,α-dimethylbenzyl cyanide) are first mixed. The mixture is heated to more than about 100°, while stirring. A mixture of $C_4$- and $C_5$-alcohol can also be employed.

After an appropriate reaction time, the reaction mixture is cooled and α,α-dimethylphenylacetic acid is precipitated out with an acid. The α,α-dimethylphenylacetic acid is isolated, for example, by crystallization or extraction. The crystallization is promoted by cooling of the suspension and/or further evaporation of the solvent. The extraction takes place by addition of organic solvents to the α,α-dimethylphenylacetic acid, for example, toluene.

The term $C_4$- and $C_5$-alcohol is understood to include, for example, n-butanol, 2-methyl-1-propanol, n-pentanol, 2-pentanol, 3-pentanol, 2-methyl-2-butanol, 3-methyl-2-butanol, 2-methyl-3-butanol, 3-methyl-1-butanol or 2-methyl-1-butanol.

The term sodium hydroxide is understood to include caustic soda in solid form or in the form of alkaline solutions of various concentrations. The water present in the alkaline solution is then included in the calculation when preparing the hydrolysis mixture.

Suitable acids are, for example, hydrochloric acid, sulfuric acid, nitric acid, or phosphoric acid, or mixtures of the acids.

About 120 mol to about 250 mol of water, for example, and about 150 mol to about 300 mol of sodium hydroxide, for example, may be used per 100 mol of the compound of the formula II for the hydrolysis reaction. The amount of $C_4$- or $C_5$-alcohol used is in general about 0.5 kg to about 1.5 kg per kg of the compound of the formula II, for example about 0.6 kg to about 1.0 kg.

The reaction time is in general from about 2 to about 6 hours, depending on the composition of the mixture and the temperature range chosen. The reaction temperature may be up to about 140° C., for example about 110° C. to about 130°

C., depending on the $C_4$- or $C_5$-alcohol used. It will be appreciated that temperatures set forth herein are approximate because the most desirable in any given situation may depend upon the reactants used and the economically acceptable process times and yields. It is within the skill of one in the art to vary these conditions in light of the economically acceptable realities of manufacture.

The by-product 2-phenyl-2-methylpropionamide has been found to be present in the isolated α,α-dimethylphenylacetic acid in an amount of less than 0.1%, based on the compound of the formula I. The residual content of the starting substrate of the compound of the formula II (α,α-dimethylbenzyl cyanide) has not been detectable in the isolated α,α-dimethylphenylacetic acid.

The starting substances for the hydrolysis reaction according to the invention can be prepared by processes known from the literature. The process product is suitable for the preparation of a large number of secondary products, for example, for the preparation of medicaments having an antiallergic action, such as 4-[4-[4-(hydroxydiphenyl)-1-piperidinyl]-1-hydroxybutyl]-α,α-dimethylphenyl acetic acid as described in U.S. Pat. No. 4,254,129.

The very short reaction times, the omission of additional purification steps, the high yields, and the high purity of the product prepared are advantageous. The substantially complete conversion into the compound of the formula I and a total content of by-products cf less than 0.1% are an advantage of the process according to the invention.

EXAMPLE 1

Preparation of α,α-dimethylphenylacetic acid 150 g of n-butanol, 65 g of water, 150 g of caustic soda, and 221 g of dimethylbenzyl cyanide (about 98.2% pure) were initially introduced into a stirring apparatus. The mixture was heated up to 120° C. to 126° C., with thorough stirring, and allowed to after-react at this temperature for about 6 hours. 250 ml of water were then added and the n-butanol was removed from the reaction mixture by distillation. After addition of a further 500 ml of water, the mixture was cooled to 30° C. to 50° C. The free dimethylphenylacetic acid was precipitated out by addition of about 433 g of hydrochloric acid having about 30% strength. This free acid could be either isolated, or extracted from the crystal suspension. During the isolation, the suspension was cooled further, and when the crystallization process had ended, the crystals were filtered off by suction and washed with cold water until free from chloride ions. After drying in a vacuum drying cabinet, a yield of 238.4 g (97.3% of theory) was obtained. The content of dimethylphenylacetic acid according to HPLC was more than 99.9%, i.e., the amide content was less than 0.1%.

The melting point of the α,α-dimethylphenylacetic acid prepared in this way was 81.5° C., as the minimum of the differential scanning calorimetry method recorded.

EXAMPLE 2

Alternatively, the α,α-dimethylphenylacetic acid can be extracted using an organic solvent (for example toluene). In this procedure, the α,α-dimethylphenylacetic acid formed is converted into the organic phase to the extent of more than 99%; the aqueous phase is separated off. The organic phase can then be employed directly for secondary reactions (for example, esterification).

HPLC Determination

Sample preparation: Dissolve 10 mg of substance in 10 ml of a mixture of acetonitrile and water (4:6).

Column:
  0.15 m length
  4.6 mm diameter
Stationary phase:
  SB-phenyl on silica gel, 5 μm, Zorbax®
Mobile phase:
  30% of acetonitrile
  70% of phosphate buffer, pH 2.5
Injection volume:
  10 μl
Flow rate:
  1 ml/minute
Detection:
  UV, 210 nm
Migration time:
  30 min The foregoing written description relates to various embodiments of the present invention, and is not intended to impose any limits on the scope of the invention or its equivalents. Numerous changes and modifications may be made therein without departing from the spirit and scope of the invention as defined in the following claims.

We claim:

1. A process for preparing the compound of the formula I:

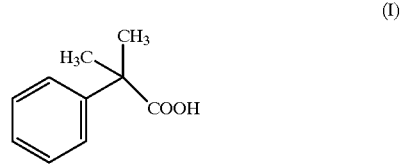

which comprises the steps of
(a) reacting a compound of the formula II:

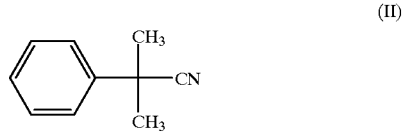

in the presence of water, sodium hydroxide, and at least one $C_4$- or $C_5$-alcohol, at a temperature of more than 100° C. to give the corresponding carboxylic acid salt; and (b) adding an acid to the carboxylic acid salt to obtain the compound of the formula I.

2. A process as claimed in claim 1, wherein the $C_4$- or $C_5$-alcohol is chosen from n-butanol, 2-methyl-1-propanol, n-pentanol, 2-pentanol, 3-pentanol, 2-methyl-2-butanol, 3-methyl-2-butanol, 2-methyl-3-butanol, 3-methyl-1-butanol, and 2-methyl-1-butanol.

3. A process as claimed in claim 1, wherein the at least one $C_4$- or $C_5$-alcohol is n-butanol.

4. A process as claimed in claim 1, wherein the compound of formula II is reacted in the presence of a mixture of $C_4$- and $C_5$-alcohols.

5. A process as claimed in claim 1, wherein the sodium hydroxide is in the form of a solid or is present in an aqueous solution.

6. A process as claimed in claim 1, wherein the acid added to the carboxylic acid salt is hydrochloric acid, sulfuric acid, nitric acid, phosphoric acid, or a mixture of two or more of hydrochloric acid, sulfuric acid, nitric acid, and phosphoric acid.

7. A process as claimed in claim 1, wherein the acid added to the carboxylic acid salt is hydrochloric acid.

8. A process as claimed in claim 1, whenrin the compound of the formula II is reacted in the presence of about 120 mol to about 250 mol of water and about 150 mol to about 300 mol of sodium hydroxide per 100 mol of the compound of the formula II.

9. A process as claimed in claim 1, wherein the compound of the formula 11 is reacted in the presence of about 0.5 kg to about 1.5 kg of the at least one $C_4$- or $C_5$-alcohol per 1 kg of the compound of the formula II.

10. A process as claimed in claim 1, wherein the compound of the formula II is reacted in the presence of about 0.5 kg to about 1.5 kg of a mixture of $C_4$- and $C_5$-alcohols per 1 kg of the compound of the formula II.

11. A process as claimed in claim 1, wherein the compound of the formula II is reacted in the presence of about 0.6 kg to about 1.0 kg of the at least one $C_4$- or $C_5$-alcohol per 1 kg of the compound of the formula II.

12. A process as claimed in claim 1, wherein the compound of the formula II is reacted in the presence of about 0.6 kg to about 1.0 kg of a mixture of $C_4$- and $C_5$-alcohols per 1 kg of the compound of the formula II.

13. A process as claimed in claim 1, wherein the reaction of the compound of the formula II is performed at a temperature of up to about 140° C.

14. A process as claimed in claim 1, wherein the reaction of the compound of the formula II is performed at a temperature of about 110° C. to about 130° C.

15. A process for preparing the compound of the formula I:

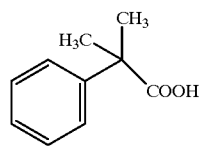

(I)

which comprises the steps of
 (a) reacting a compound of the formula II:

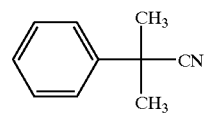

(II)

in the presence of about 120 mol to about 250 mol of water and about 150 mol to about 300 mol of sodium hydroxide per 100 mol of the compound of the formula II, and about 0.6 kg to about 1.0 kg of at least one $C_4$- or $C_5$-alcohol per 1 kg of the compound of the formula II, at a temperature of about 110° C. to about 130° C. to give the corresponding carboxylic acid salt; and
 (b) adding an acid to the carboxylic acid salt to obtain the compound of the formula I.

16. A process as claimed in claim 15, wherein the at least one $C_4$- or $C_5$-alcohol is n-butanol, and wherein the acid added to the carboxylic acid salt is hydrochloric acid.

* * * * *